United States Patent [19]
Lemoine et al.

[11] Patent Number: 5,631,144
[45] Date of Patent: May 20, 1997

[54] APPLICATION OF NOVEL DNA FRAGMENTS AS A CODING SEQUENCE FOR A SIGNAL PEPTIDE FOR THE SECRETION OF MATURE PROTEINS BY RECOMBINANT YEAST, EXPRESSION CASSETTES, TRANSFORMED YEAST AND CORRESPONDING PROCESS FOR THE PREPARATION OF PROTEINS

[75] Inventors: Yves Lemoine, Strasbourg; Martine Nguyen, Wittersheim, both of France; Tilman Achstetter, Oberkirch, Germany; Jean-Marc Reichhart, Strasbourg, France

[73] Assignee: Transgene S.A., Courbevoie, France

[21] Appl. No.: 385,375

[22] Filed: Feb. 7, 1995

Related U.S. Application Data

[63] Continuation of Ser. No. 178,356, Jan. 4, 1994, abandoned, which is a continuation of Ser. No. 32,175, Mar. 15, 1993, abandoned, which is a continuation of Ser. No. 623,900, filed as PCT/FR90/00306, Apr. 27, 1990, abandoned.

[30] Foreign Application Priority Data

Apr. 28, 1989 [FR] France .................. 89 05687
Apr. 27, 1990 [WO] WIPO .............. PCT/FR90/00306

[51] Int. Cl.$^6$ .................. C12N 1/19; C12N 5/10; C12N 15/63; C12N 15/81
[52] U.S. Cl. .............. 435/69.9; 435/252.3; 435/254.2; 435/320.1; 435/325; 536/23.1
[58] Field of Search ................. 435/69.1, 69.2, 435/69.8, 172.3, 320.1, 254.11, 254.21, 69.9, 240.2, 240.4, 252.3, 254.2; 536/24.1, 23.1; 935/28, 37, 48

[56] References Cited

U.S. PATENT DOCUMENTS 5,087,613 2/1992 Courtney ................... 514/12

FOREIGN PATENT DOCUMENTS

| 0158564 | 10/1985 | European Pat. Off. . |
|---|---|---|
| 0200655 | 11/1986 | European Pat. Off. . |
| 0225633 | 6/1987 | European Pat. Off. . |
| 0252854 | 1/1988 | European Pat. Off. . |
| 0273800 | 7/1988 | European Pat. Off. . |
| 0349451 | 3/1990 | European Pat. Off. . |

OTHER PUBLICATIONS

Ernst, J.F. *DNA* 7(5): 355–360 (1988).

Gabrielsen, O.S. "Efficient secretion of human parathyroid hormon by *S cerevisiae*." *Gene* 90: 255–262 (1990).

*The Journal of Biological Chemistry*, vol. 257, No. 24, 25 Dec. 1982 American Society of Biological Chemists, Inc., (Baltimore, MD), J. Kaput et al., "Nucleotide sequence of the yeast nuclear gene for cytochrome c peroxidase precursor", pp. 15054–1058.

*Journal of Bacteriology*, vol. 171, No. 11, Nov. 1989, American Society for Microbiology, (Baltimore, MD), F. Klebl et al., "Molecular cloning of a cell wall exo–β–1, 3–glucase from *Saccharomyces cerevisiae*", pp. 6259–6264.

*Primary Examiner*—Dian C. Jacobson
*Attorney, Agent, or Firm*—Burns, Doane, Swecker & Mathis, L.L.P.

[57] ABSTRACT

The invention relates to new DNA fragments and to their application as a DNA coding fragment for a signal peptide which can be used for the secretion of proteins, said peptide including a sequence of amino-acids which show a degree of correspondence of at least 60% with the sequence of amino-acids (I) or (II), preferably with the sequence (II). The sequences (I) and (II) are as follows: (I) Arg-Phe-Ser-Thr-Thr-Leu-Ala-Thr-Ala-Ala-Thr-Ala-Leu-Phe-Phe-Thr-Ala-Ser-Gln. (II) Arg-Phe-Ser-Thr-Thr-Leu-Ala-Thr-Ala-Ala-Thr-Ala-Leu-Phe-Phe-Thr-Ala-Ser-Gln-Val-Ser-Ala.

25 Claims, 4 Drawing Sheets

FIG_1
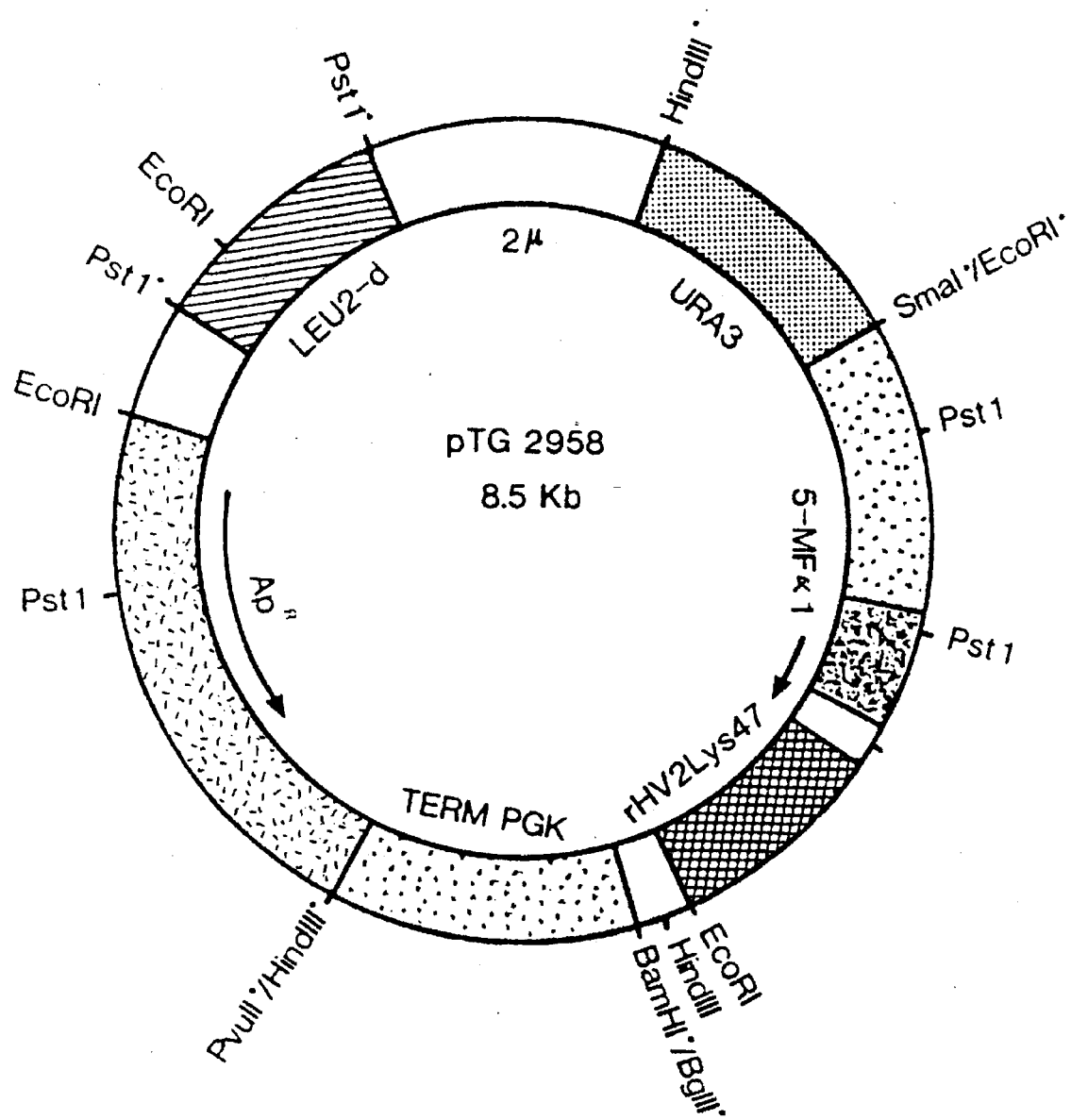

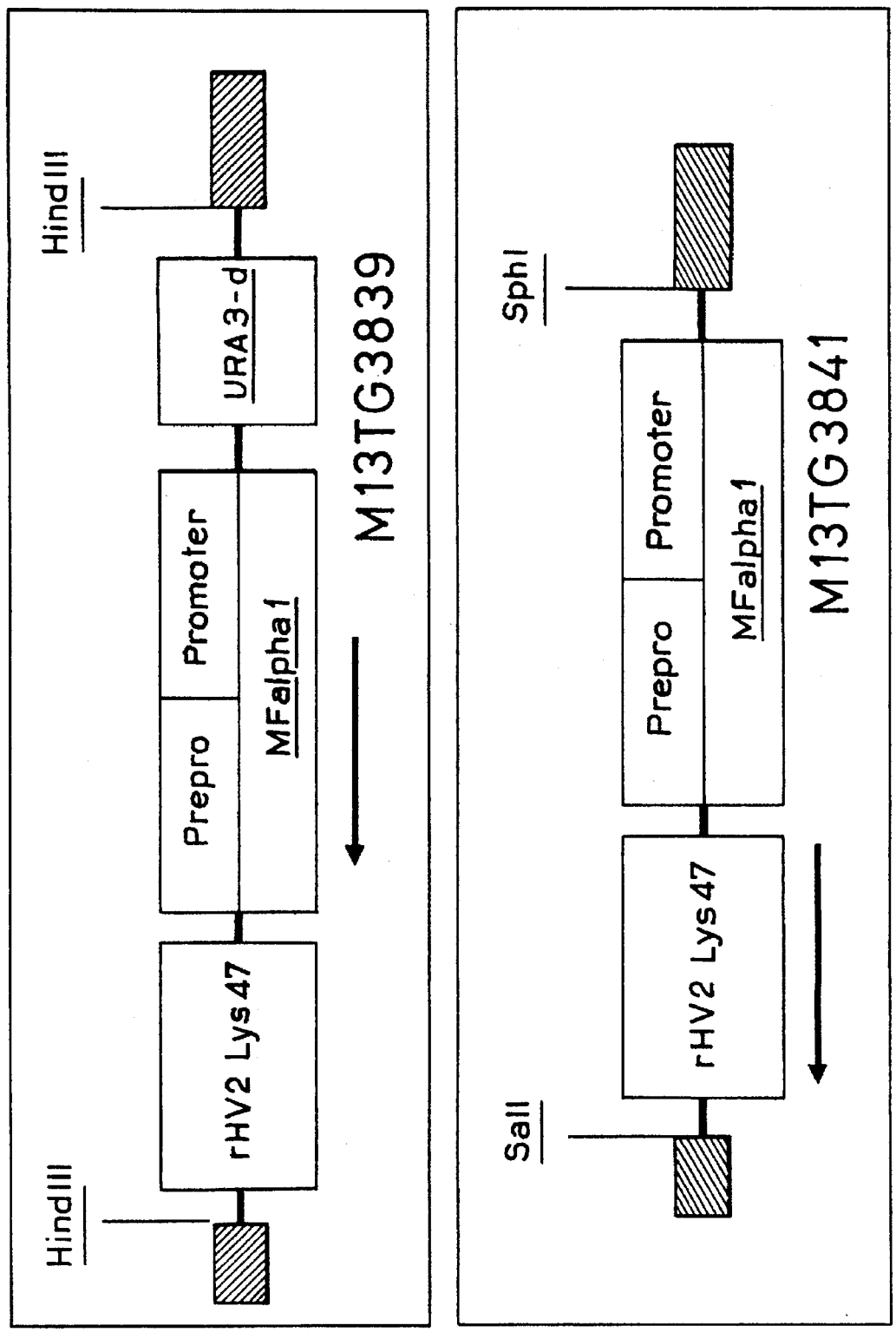
FIG_2

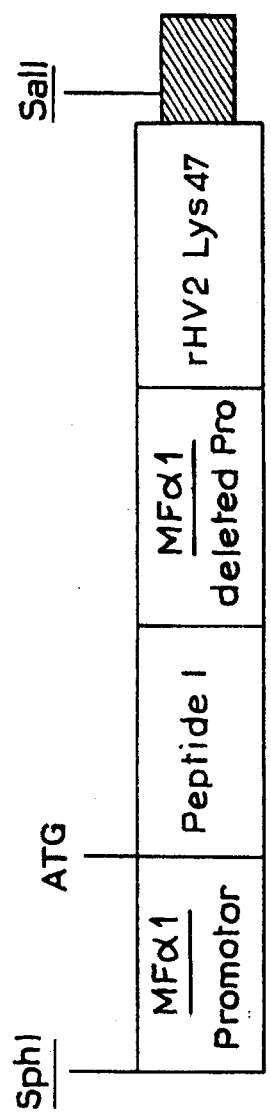

APPLICATION OF NOVEL DNA FRAGMENTS AS A CODING SEQUENCE FOR A SIGNAL PEPTIDE FOR THE SECRETION OF MATURE PROTEINS BY RECOMBINANT YEAST, EXPRESSION CASSETTES, TRANSFORMED YEAST AND CORRESPONDING PROCESS FOR THE PREPARATION OF PROTEINS

This application is a continuation of application Ser. No. 08/178,356 filed Jan. 4, 1994, now abandoned, which is a continuation of application Ser. No. 08/032,175 filed Mar. 15, 1993, now abandoned, which is a continuation of application Ser. No. 07/623,900, filed as PCT/FR90/00306 Apr. 27, 1990, now abandoned.

The present invention relates to novel DNA fragments and to their use as DNA fragments coding for a signal peptide useful for the secretion of heterologous proteins by eukaryotic (animal or plant) or prokaryotic (bacterial) cells, more especially yeasts such as Saccharomyces strains.

During the preparation of a heterologous protein by recombinant DNA techniques, one of the objectives often pursued is the production of a product which is secreted into the culture medium of cells which synthesize the heterologous protein. In effect, in the case, in particular, of the preparation of a protein of industrial interest intended for production in large quantities, it is desirable, in order that it retains the desired properties, for the protein to be produced in mature form, that is to say devoid of any amino acid or additional peptide sequence remaining fused to the protein. Moreover, it can be advantageous for it to be secreted into the culture medium in order to facilitate the recovery and purification operations.

The proteins which are secreted by a cell, especially a eukaryotic cell, are very generally synthesized in the form of a polypeptide precursor comprising a fragment corresponding to the mature protein (active form) and an N-terminal fragment known as a "pre" fragment, also referred to as a signal peptide, which participates in the mechanism of secretion of the protein by the cell. In addition, this polypeptide precursor can comprise one or more additional fragments referred to as "pro" fragments. In the latter case, the polypeptide precursor is referred to as a "prepro" precursor or first precursor. A "pro" fragment is, in the majority of cases, inserted between the signal peptide and the fragment corresponding to the mature protein, although this is not an absolute rule.

A signal peptide initiates (i) insertion of the protein into the cell membrane, (ii) translocation of the protein through the cell membrane or (iii) entry of the protein into the endoplasmic reticulum of the cell for the purpose of secretion of the protein via the endoplasmic reticulum. Once the signal peptide has fulfilled its function, it is normally detached by proteolytic cleavage to liberate a mature protein or a second precursor referred to as a "pro" precursor which, like the first precursor, has no biological activity or which does not have the complete biological activity of the mature protein.

A "pro" fragment is useful inasmuch as it blocks or modifies the activity of the protein, thereby enabling the cell to be protected against possible toxic effects of the protein, or the protein to be protected against possible modifications or degradations. It can also participate to some extent in the mechanism of secretion. At the end of the secretion process, the "pro" fragment of the second precursor is detached by proteolytic cleavage to liberate a mature protein (active form).

At the junction of the "pre" fragment and the "pro" fragment, as well as at the junction of the "pro" fragment and the fragment corresponding to the mature protein, there should be a proteolytic cleavage site which is recognized by one of the proteases of the cell in which the protein is synthesized. This proteolytic cleavage site generally consists of a sequence of 2 or 3 or more amino acids (hereinafter referred to as a proteolysis sequence) which is accessible to the protease in the "pro" precursor and which, if it exists in the fragment corresponding to the mature protein, is not accessible. On the face of it, three cases are possible, illustrated below with reference to the junction of the "pre" and "pro" fragments:

either the protease cuts at the beginning of the sequence, and the proteolysis sequence must accordingly be read on the "pro" fragment;

or the protease cuts at the end of the sequence, and the proteolysis sequence must accordingly be read on the "pre" fragment;

or the protease cuts in the middle of the sequence, and the proteolysis sequence must accordingly be read straddling the "pre" and "pro" fragments.

These considerations naturally apply in a similar manner to the cleavage site situated at the junction of the "pro" fragment and the fragment corresponding to the mature protein.

For the construction of synthetic precursors by genetic engineering methods, a possible approach is to use natural fragments (that is to say as found in nature) and to insert at the appropriate place a new proteolytic cleavage site, or some amino acids so as to re-form a new proteolytic cleavage site in combination with the fragments, this new cleavage site being, of course, recognized by one of the proteases of the cell in which the synthetic precursor is expressed.

An example of the type of synthesis and the method of secretion described above is illustrated by the case of the α sex pheromone S. cerevisiae yeast, also referred to as α factor (encoded from the MFα1 or MFα2 gene). α factor is, in effect, synthesized in the form of a "prepro" precursor as described in Kurjan and Herskowitz, Cell (1982) 30: 933. The amino acid sequence of the "pre" fragment of the precursor of α factor is [SEQ ID NO.:1] Met Arg Phe Pro Ser Ile Phe Thr Ala Val Leu Phe Ala Ala Ser Ser Ala Leu Ala, while that of the "pro" fragment of the precursor of α factor is [SEQ ID NO.:2] Ala Pro Val Asn Thr Thr Thr Glu Asp Glu Thr Ala Gln Ile Pro Ala Glu Ala Val Ile Gly Tyr Ser Asp Leu Glu Gly Asp Phe Asp Val Ala Val Leu Pro Phe Ser Asn Ser Thr Asn Asn Gly Leu Leu Phe Ile Asn Thr Thr Ile Ala Ser Ile Ala Ala Lys Glu Glu Gly Val Ser Leu Asp.

Surprisingly, it has now been found that the N-terminal end of the precursor of a yeast enzyme, this N-terminal end having the amino acid sequence: [SEQ ID NO.:3] Arg-Phe-Ser-Thr-Thr-Leu-Ala-Thr-Ala-Ala-Thr-Ala-Leu-Phe-Phe-Thr-Ala-Ser-Gln-Val-Ser-Ala, may be used by way of a signal peptide for the secretion of heterologous proteins, as well as different variants of this N-terminal end. "Heterologous protein" means a protein which is not naturally produced by the host cell, or alternatively which is encoded by a sequence which does not originate from the host cell.

In accordance with this, the subject of the present invention is an isolated DNA fragment which codes for a peptide whose amino acid sequence exhibits an at least 60%, and preferably at least 80%, degree of homology with the amino acid sequence (I) or (II), and preferably with the sequence (II). The sequences (I) [SEQ ID NO.:4] and (II) [SEQ ID NO.:3] are as follows:

Arg-Phe-Ser-Thr-Thr-Leu-Ala-Thr-Ala-Ala-Thr-Ala-Leu-Phe-Phe-
Thr-Ala-Ser-Gln. (I)

Arg-Phe-Ser-Thr-Thr-Leu-Ala-Thr-Ala-Ala-Thr-Ala-Leu-Phe-Phe-
Thr-Ala-Ser-Gln-Val-Ser-Ala. (II)

"Isolated DNA fragment" means a DNA fragment whose 3' end is not linked via a covalent bond to a DNA fragment coding for an enzyme having β-1,3-glucanase activity as described, in particular, in Klebl & Tanner, J. Bact, November 1989, 171: 6259.

More especially, a DNA fragment according to the invention codes for a peptide comprising the following amino acid sequence (III) [SEQ ID NO.:5]:

$R_1—R_2—R_3$—Thr—Thr—$R_4$—Ala—Thr—Ala—Ala—Thr—Ala—Leu—Phe—Phe—Thr—Ala—$R_5$—$R_6$ (III)
1          5          10          15      19 in which:

$R_1$ is an amino acid selected from Arg and Lys, $R_2$ and $R_6$ are each an amino acid selected independently from Ala, Asn, Cys, Gln, Gly, His, Ile, Leu, Met, Phe, Pro, Ser, Thr, Trp, Tyr and Val, $R_3$ and $R_5$ are each an amino acid selected independently from Asp, Gly, Asn, Pro and Ser, and $R_4$ is an amino acid selected from Val, Leu, Ala, Cys, Phe, Ile and Met.

Preferably, a DNA fragment according to the invention codes for a peptide comprising the following amino acid sequence (IV) [SEQ ID NO.:6]:

$R_1$-$R_2$-$R_3$-Thr-Thr-$R_4$-Ala-Thr-Ala-Ala-Thr-Ala-Leu-Phe-Phe-Thr-Ala-$R_5$-$R_6$-$R_7$ (IV)

in which:

$R_1$ is an amino acid selected from Arg and Lys, $R_2$ and $R_6$ are each an amino acid selected independently from Ala, Asn, Cys, Gln, Gly, His, Ile, Leu, Met, Phe, Pro, Ser, Thr, Trp, Tyr and Val, $R_3$ and $R_5$ are each an amino acid selected independently from Asp, Gly, Asn, Pro and Ser, $R_4$ is an amino acid selected from Val, Leu, Ala, Cys, Phe, Ile and Met, and $R_7$ is a proteolysis sequence.

$R_7$ is preferably a proteolysis sequence $R_8$-$R_9$-$R_{10}$
in which:

$R_8$ is an amino acid selected from Ala, Val, Ser, Cys, Gly, Ile, Leu and Thr, $R_9$ is an amino acid selected from Ala, Arg, Cys, Gln, Gly, His, Ile, Leu, Met, Phe, Pro, Ser, Thr, Trp, Tyr and Val and $R_{10}$ is an amino acid selected from Ala, Cys, Gly, Leu, Pro, Gln, Ser and Thr.

According to the invention, a preferred DNA fragment codes for a peptide comprising an amino acid sequence selected from the following amino acid sequences (V) [SEQ ID NO.:4], (VI) [SEQ ID NO.:7], (VII) [SEQ ID NO.:8], and (VIII) [SEQ ID NO.:9]:

Arg-Phe-Ser-Thr-Thr-Leu-Ala-Thr-Ala-Ala-Thr-Ala-Leu-Phe-Phe-
Thr-Ala-Ser-Gln (V)

Arg-Phe-Ser-Thr-Thr-Val-Ala-Thr-Ala-Ala-Thr-Ala-Leu-Phe-Phe-
Thr-Ala-Ser-Gln (VI)

Arg-Phe-Ser-Thr-Thr-Leu-Ala-Thr-Ala-Ala-Thr-Ala-Leu-Phe-Phe-
Thr-Ala-Ser-Gln-$R_7$ (VII)

in which $R_7$ is defined as above.

Arg-Phe-Ser-Thr-Thr-Val-Ala-Thr-Ala-Ala-Thr-Ala-Leu-Phe-Phe-
Thr-Ala-Ser-Gln-$R_7$ (VIII)

in which $R_7$ is as defined above.

As a matter of absolute preference, $R_7$ is a sequence in which $R_8$ is Val, $R_9$ is Ser and $R_{10}$ is Ala.

As a matter of very special preference, a DNA fragment according to the invention has as its nucleotide sequence one of the following sequences (IX) [SEQ ID NO.:10], (X) [SEQ ID NO.:11], (XI) [SEQ ID NO.:12] and (XII) [SEQ ID NO.:13]:

(IX)
CGT TTC TCT ACT ACA GTC GCT ACT GCA GCT ACT GCG
CTA TTT TTC ACA GCC TCC CAA, (X)
CGT TTC TCT ACT ACA CTC GCT ACT GCA GCT ACT GCG
CTA TTT TTC ACA GCC TCC CAA, (XI)
CGT TTC TCT ACT ACA GTC GCT ACT GCA GCT ACT GCG
CTA TTT TTC ACA GCC TCC CAA GTT TCA GCT, (XII)
CGT TTC TCT ACT ACA CTC GCT ACT GCA GCT ACT GCG
CTA TTT TTC ACA GCC TCC CAA GTT TCA GCT.

The peptides encoded by the DNA fragments according to the invention comprise a hydrophobic region possessing an α-helical structure between the amino acid at position 3 and the amino acid at position 18. This structure contributes to making them suitable for use as a signal peptide. The hydrophobic portion of signal sequences is known to be composed predominantly of the amino acids Ala, Cys, Phe, Ile, Leu, Met and Val. It is hence also possible to predict that some modifications of amino acids will not bring about a modification in the capacity of the signal peptide to play its part.

In another aspect, the invention accordingly proposes the application of a DNA fragment according to the invention by way of a DNA fragment coding for a signal peptide useful for the secretion of a heterologous protein by a host cell in which the heterologous protein is synthesized. Generally speaking, the invention may be implemented in a prokaryotic or eukaryotic cell, and preferably in the latter. The eukaryotic cell can be, for example, a mammalian or yeast cell. As a matter of absolute preference, the secretion of a heterologous protein using a signal peptide encoded by a fragment according to the invention is carried out by a yeast cell, for example of the genus Saccharomyces, more especially of the species S. cerevisiae.

Naturally, as DNA fragments coding for a signal peptide, the DNA fragments according to the invention will be preceded by a translation initiation codon, generally a codon coding for a methionine, especially an ATG.

The DNA fragments according to the invention may be used for the construction of a cassette for the expression of a protein, the fragments being preceded by the initiation codon and being alone or in combination with other components, for example a "pro" fragment. These DNA fragments may be prepared by chemical synthesis, by means of an oligonucleotide synthesizer by a technique known to those skilled in the art.

The invention also relates to a cassette for the expression of a heterologous protein comprising a DNA fragment according to the invention by way of a DNA fragment coding for the signal peptide of the said heterologous protein. Specifically, an expression cassette according to the invention, which hence contains the information needed for the secretion of a mature heterologous protein, comprises sequentially at least:

a) a DNA fragment containing transcription and translation initiation signals, b) a DNA fragment according to the invention, and c) a DNA fragment coding for a mature heterologous protein (with translation termination codon).

In a first variant, the fragment b) may be fused directly in frame with the fragment c), insofar as, at the junction of the fragment b) and the fragment c), there is a DNA sequence coding for a proteolytic cleavage site so as to permit the liberation of a mature protein at the end of the process of expression and secretion. Preferably, the DNA sequence coding for a proteolytic cleavage site is read on the fragment b).

In a second variant, an expression cassette according to the invention comprises, in addition, a DNA fragment b') coding for a "pro" peptide fragment. This fragment b') is fused in frame with the fragment b) and the fragment c), insofar as, at the junction of the fragments b) and b') on the one hand and of the fragments b') and c) on the other hand, there is a DNA sequence coding for a proteolytic cleavage site.

A large number of fragments b') may be used in the cassettes according to the invention. In particular, various fragments b') may be constructed synthetically. By way of example, the construction of a synthetic fragment b') from the DNA sequence coding for the "pro" fragment of the precursor of α factor is described below. This sequence may be used in whole or in part. In a particular embodiment, this sequence is used after deletion of the portion coding for the amino acids at positions 3 to 42 in the "pro" fragment; that is to say the sequence [SEQ ID NO.:14] coding for: Ala Pro Gly Leu Leu Phe Ile Asn Thr Thr Ile Ala Ser Ile Ala Ala Lys Glu Glu Gly Val Ser Leu Asp. To form the fragment b'), the latter DNA sequence is followed by a sequence coding for (i) a peptide comprising a proteolytic cleavage site, or (ii) a proteolytic cleavage site, the latter embodiment being preferred. Most especially, the latter cleavage site is Lys-Arg or Arg-Arg, this being recognized by yeast yscF endopeptidase which is encoded by the KEX2 gene and which cuts at the C-terminal end of the dipeptide Lys-Arg or Arg-Arg. In summary, a particular fragment b') [SEQ ID NO.:15] codes for Ala Pro Gly Leu Leu Phe Ile Asn Thr Thr Ile Ala Ser Ile Ala Ala Lys Glu Glu Gly Val Ser Leu Asp Lys Arg.

The sequence a) comprises, in particular, a promoter which is functional in the cell in which it is desired to synthesize the heterologous protein encoded by the fragment c), preferably a promoter which is functional in yeast. There may be mentioned, for example, constitutive promoters of yeast whose functionality has been confirmed by the transcription of genes coding for heterologous proteins such as the PGK, ENO1 and MFα1 promoters, or alternatively, inducible promoters such as PHO5 and GAL1. For example, when elements of the MFα1 gene of yeast are used in the expression cassette, the promoter of the MFα1 gene may be used.

Finally, the expression cassettes can also comprise a DNA fragment d) containing transcription termination signals which are preferably functional in yeast, for example that of the PGK gene.

Generally speaking, an expression cassette according to the invention may be introduced into a prokaryotic or eukaryotic cell, preferably a eukaryotic cell such as a mammalian or yeast cell; a yeast cell being most especially preferred. This introduction may be carried out by placing the cassette in an autonomously replicating plasmid, or in a construction intended for integration which is to be introduced directly into the genome of the yeast, so as to obtain, in both cases, a transformed cell.

When the plasmid is autonomous, it will contain elements providing for its distribution and its replication; for example, an origin of replication such as that of the 2μ plasmid of yeast. In addition, the plasmid may contain selectable elements such as the URA3 or LEU2 gene, which provide for the complementation of ura3 or leu2 yeast. In particular, the URA3 gene from its promoter has been deleted (URA3-d) may advantageously be used.

These plasmids may also contain elements providing for their replication in bacteria, when the plasmid has to be a shuttle plasmid, for example an origin of replication such as that of pBR322, a selectable marker gene such as $Amp^R$ and/or other elements known to those skilled in the art.

In keeping with the foregoing, the present invention also relates to a cell transformed by (i) a DNA fragment according to the invention, or (ii) an expression cassette according to the invention, either inserted into a plasmid or integrated in the genome of the cell.

When the promoter is that of the MFα1 gene, the transformed yeast cell is preferably of the MATα mating type. For example, a strain of genotype ura3 or leu2 or the like, complemented by the plasmid to provide for maintenance of the plasmid in the yeast by a suitable selection pressure, will be used.

Finally, the subject of the invention is a process for the preparation of a heterologous protein, characterized in that a cell according to the invention is cultured and in that the said protein is recovered in the culture medium. This process applies to the preparation of any protein of heterologous nature. Among these proteins, hirudin or defensins, for example defensin A, may be mentioned in particular.

More especially, the invention relates to a process for the secretion of hirudin in mature form from transformed yeast strains according to the invention.

The invention applies most especially well to the production of hirudin; for this reason, one of the examples illustrating the invention relates to this protein. In effect, hirudin, the main source of which is in the salivary glands of medicinal leeches, is a very specific and very effective inhibitor of thrombin. It is hence a very advantageous therapeutic agent whose clinical use demands a very high purity of the product, and which is hence an advantageous candidate for production by genetic engineering.

A number of natural variants of hirudin have been identified, designated HV1, HV2 and HV3. Subsequently, these natural variants, as well as other, analogous ones, have been prepared by genetic engineering in various host cells, as is described, for example, in the European patent publications EP-A-0,200,655 and EP-A-0,273,800 in the name of the Applicant. Comparison of the hirudin synthesized by *Escherichia coli* (*E. coli*) and by *S. cerevisiae* has shown that the hirudin synthesized by *E. coli* remains intracellular and must hence be purified from a very large number of *E. coli* polypeptides. It is hence especially advantageous to be able to cause a hirudin gene to be expressed in yeast so as to obtain a hirudin secreted in mature form, and without the yeast producing substances which are pyrogenic or toxic with respect to man.

The invention hence applies to all hirudin molecules, that is to say natural variants of hirudin as they are or which have undergone one or more mutations while retaining their antithrombotic activity, the latter type of variant being referred to as an analog. The examples below will relate more especially to the analog designated rHV2Lys47 (for recombinant variant HV2 which has undergone a mutation of the amino acid Asp at position 47 to the amino acid Lys), described in the patent publication EP-A-0,273,800 already mentioned.

The invention also applies to the production of defensins. Defensins, also known as phormicins, are peptides originally extracted from the hemolymph of certain insects, Diptera, which have a bactericidal activity on Gram-positive microorganisms. These defensins are more fully described in European Patent Application EP-A-349,451. Defensin A is a basic peptide having as its sequence Ala Thr Cys Asp Leu Leu Ser Gly Thr Gly Ile Asn His Ser Ala Cys Ala Ala His Cys Leu Leu Arg Gly Asn Arg Gly Gly Tyr Cys Asn Gly Lys Gly Val Cys Val Cys Arg Asn. Defensin B differs from defensin A only in the amino acid at position 32, where an arginine replaces a glycine.

The examples below will enable other features and advantages of the present invention to be demonstrated. These examples will be illustrated by the following figures:

BRIEF DESCRIPTION OF THE DRAWINGS

FIG. 1 shows the diagrammatic structure of plasmid pTG2958.

FIG. 2 shows the diagrammatic structure of the vectors M13TG3839 and M13TG3841. For M13TG3839, the shaded boxes at the ends correspond to M13TG103, and for M13TG3841 to M13TG3149.

FIG. 3 shows the diagrammatic structure of the vector M13TG3845. The shaded box corresponds to M13TG3149. Peptide 1 has the amino acid sequence of Formula 1 (SEQ ID NO:4).

FIG. 4 shows the diagrammatic structure of plasmid pTG3828.

EXAMPLE 1

Figure 5:
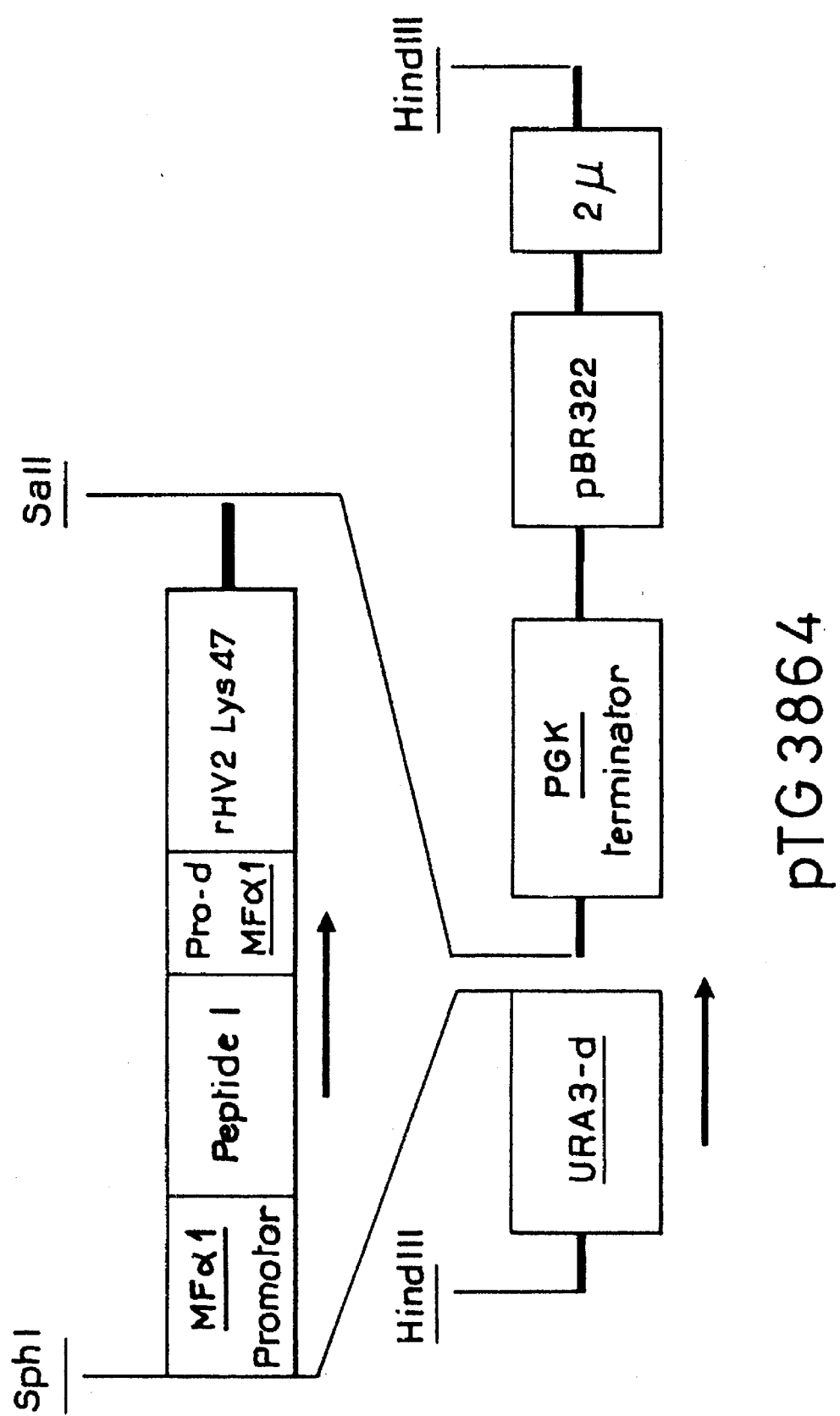
FIG. 5 shows the diagrammatic structure of plasmid pTG3864.

Construction of the Vectors for the Expression of Hirudin: pTG3864, pTG3867, pTG3894 and pTG3884

A. Construction of vector M13TG3845

Plasmid pTG2958 (FIG. 1) differs little from plasmid pTG1833, described in the European patent publication EP-A-252,854, carrying the coding sequence for rHV2Asp47. Plasmid pTG2958 does not contain the artificially introduced HindIII restriction site. Plasmid pTG2958 contains:

a fragment of 1217 base pairs corresponding to the 5' region of the MFα1 gene (containing the promoter, the sequence coding for the signal peptide, the "pro" region and a sequence coding for the peptide Lys-Arg), and 4 base pairs (BglII° site, Klenow treatment), a fragment of 234 base pairs containing the complementary DNA of rHV2Lys47, a fragment of 243 base pairs comprising the PGK terminator of yeast, the PvuII-EcoRI fragment of pBR322 comprising, inter alia, the origin of replication of this plasmid and the ampicillin resistance gene (2292 base pairs), the EcoRI-HindIII fragment of the 2μ plasmid of yeast (B form), containing the LEU2 gene of yeast in deleted form inserted into the PstI site, a HindIII-SmaI fragment of the URA3 gene of yeast.

The NcoI-NcoI fragment of the vector pTG2958 which carries the LEU-2d, 2μ and URA3 sequences is replaced by the NcoI-NcoI fragment of pTG2800, described in the European patent publication EP-A-0,268,501, which carries the sequences of the 2μ plasmid and of the URA3 gene from which its promoter has been deleted (URA3-d), to give pTG2877.

The vector M13TG3839 (FIG. 2) is derived from M13TG103 [Kieny, M. P. et al. (1983) Gene 26, 91–99] in which the HindIII-HindIII fragment of pTG2877 is introduced into the same site. A SalI restriction site is introduced into this vector downstream from the translation termination codon of the region coding for rHV2Lys47 by directed mutagenesis using the following oligonucleotide: [SEQ ID NO.:17]

5' CAATGAAAAATGGTCGACTATCAATCATAG to give M13TG3839 SalI. A SphI restriction site is then introduced upstream from the expression cassette while removing the URA3-d sequence by directed mutagenesis using the following oligonucleotide: [SEQ ID NO.:18]

5' GACGGCCAGTAGAATTGGCATGCTAT-TGATAAGATTTAAAG to give M13TG3840.

The vector M13TG131 [Kieny M. P. et al. (1983) Gene 26 91–99] is cleaved with PstI, the ends are blunted by treatment using the Klenow fragment of DNA polymerase I and it is then religated with itself to give M13TG3160. This vector is then cleaved with SmaI and EcoRV and thereafter religated to give M13TG3149.

The SphI-SalI fragment of M13TG3840 (described above) carrying the rHV2Lys47 expression cassette (without a transcription termination sequence) is introduced into the SphI-SalI site of M13TG3149 to give M13TG3841 (FIG. 2).

The sequence coding for the amino acids at positions 3 to 42 in the "pro" fragment of the precursor of MFα1 is removed from M13TG3149 by directed mutagenesis, and a SmaI restriction site introduced using the following oligonucleotide: [SEQ ID NO.:19]

5' CTCCGCATTAGCTGCTCCCGGGTTATTGTTTATAAAT, to give what will be referred to hereinafter as a deleted "pro" sequence.

M13TG3842 is thereby obtained. A BamHI restriction site destroying the ATG of the precursor of α factor is introduced into this vector by directed mutagenesis with the following oligonucleotide: [SEQ ID NO.:20]

5' AATATAAACGATTAAAAGGATC-CGATTTCCTTCAATTTTA

M13TG3843 is then obtained. After phosphorylation, the following oligonucleotides: [SEQ ID NOS.:21–24]

5' GATCCGTTTCTCTACTACAGTCGCTACTGCAGCTACTGCGCTATT
    GCAAAGTGATGATGTCAGCGATG 5' and

5' TTTCACAGCCTCCCAAGTTTCAGCTGCTCCC
ACGTCGATGACGCGATAAAAAGTGTCGGAGGGTTCAAAGTCGACGAGGG 5' are inserted into the vector M13TG3843 cut with BamHI and SmaI, thereby introducing the sequence XI, hence without ATG. In order to restore the ATG, the BamHI site is removed by directed mutagenesis using the following oligonucleotide: [SEQ ID NO: 25]

5' AATATAAACGATTAAAAGAAT-
    GCGTTTCTCTACTACAGTC to give the vector M13TG3845 (FIG. 3), which contains:

the promoter of the MFα1 gene, followed by an ATG codon, as a fragment a), the sequence XI as a fragment b), the deleted "pro" sequence of the MFα1 gene, followed by codons coding for Lys-Arg as a fragment b'), the sequence coding for rHV2Lys47 as a fragment c), a portion of the vector M13TG3149.

B. Construction of plasmid pTG3864

Plasmid pTG848, described in the European patent publication EP-A-0,252,854, is digested with BglII and then religated to give pTG2886. The large HindIII-EcoRI fragment of pTG2886 is ligated in the presence of T4 ligase to the 2.1-kb HindIII-EcoRI fragment of plasmid pFL1 [Parent, S. A. et al. (1985) Yeast 1, 83–138], which carries the sequence of the 2μ plasmid of S. cerevisiae, to give plasmid pTG2886 LEU2-d, URA3-d. The 0.9-kb HindIII fragment of plasmid pTG2800, described in the European patent publication EP-A-0,258,501, carrying the URA3-d gene is then inserted into the HindIII site of this plasmid to give pTG2886 URA3-d, delta LEU2-d. The SmaI-BglII fragment of M13TG131 [Kieny et al. (1983) Gene 26, 91–99], which possesses several restriction sites, is then introduced into this plasmid to give pTG3828 (FIG. 4), which contains:

the sequence of the URA3 gene from which its promoter has been deleted (URA3-d), restriction sites originating from M13TG131 permitting the insertion of elements for the expression of a heterologous gene, rHV2Lys47 in the present case, the transcription terminator of the PGK gene of yeast, a fragment of pBR322 which permits replication and selection in E. coli, a fragment of the 2μ plasmid which possesses the structural elements needed for replication and mitotic equipartition in yeast.

The SphI-SalI fragment of the vector M13TG3845 (FIG. 3) is introduced into plasmid pTG3828 digested with SphI and SalI to give the expression vector pTG3864 (FIG. 5).

C. Construction of the expression vector pTG3867

To eliminate completely the sequence coding for the precursor of the MFα1 gene, a directed mutagenesis is performed on M13TG3845 (FIG. 3) using the following oligonucleotide: [SEQ ID NO.:26]

5' GCCTCCCAAGTTTCAGCTATTACGTATACAGACTGC to obtain the vector M13TG3846. The SphI-SalI fragment of this vector is introduced into plasmid pTG3828 (FIG. 4) digested with SphI and SalI to give the expression vector pTG3867. In this vector, the sequence XI and that coding for rHV2Lys47 are adjacent. To obtain the diagrammatic structure of this plasmid, it suffices to remove the deleted "pro" sequence of MFα1 in FIG. 5.

D. Construction of the expression vector pTG3894

A SmaI site is created in the sequence coding for the "pro" fragment of the precursor of α factor by directed mutagenesis on M13TG3841 (FIG. 2) by means of the following oligonucleotide: [SEQ ID NO.:27]

5' TCCGCATTAGCTGCTCCCGGGAACACTACAACAGAA to obtain M13TG3869. This vector is then digested with SphI and SmaI, and the small fragment is isolated and ligated to the large SphI-SmaI fragment of M13TG3845 (FIG. 3) to give the vector M13TG3891. The SphI-SalI fragment of this vector is introduced into plasmid pTG3828 (FIG. 4) opened at the SphI and SalI sites to give the expression vector pTG3894, which hence contains the mutated "pro" sequence of the precursor of α factor. To obtain the diagrammatic structure of this plasmid, it suffices to replace the deleted "pro" sequence of MFα1 in FIG. 5 by the mutated "pro" sequence.

E. Construction of the expression vector pTG3884

The sequence XI is modified by directed mutagenesis on M13TG3845 using the following oligonucleotide [SEQ ID NO.:28]:

5' GTTTCTCTACTACACTCGCTACTGC

The modification of a single base gives the sequence XII, and induces the replacement of a valine by a leucine as the amino acid $R_4$ of the signal peptide. The bacteriophage M13TG3846 is thereby obtained. The SphI-SalI fragment of M13TG3846 is introduced into plasmid pTG3828 (FIG. 4) opened at the SphI and SalI sites to give the expression vector pTG3884, which contains:

the sequence of the URA3 gene from its promoter has been deleted (URA3-d), the promoter of the MFα1 gene, followed by an ATG codon, as a fragment a), the sequence XII as a fragment b), the deleted "pro" sequence of the MFα1 gene, followed by the codons coding for Lys-Arg, as a fragment b'), the sequence coding for rHV2Lys47 as a fragment c), the terminator of the gene coding for PGK of yeast, a fragment of pBR322, a fragment of the 2μ plasmid.

EXAMPLE 2

Production of rHV2Lys47 in the Culture Supernatant in Relation to the Plasmid Used A yeast strain of the species Saccharomyces cerevisiae of genotype MATα, ura3-251,-373,-328, leu2-3,-112, his3, pep4-3 is transformed with plasmids pTG3864, pTG3867, pTG3894 and pTG3884 by the lithium acetate method [Ito, H. et al. J. Bactériol. (1983) 153: 163] and the Ura+ prototrophs are selected. They are then cultured in an Erlenmeyer at 30° C. on a selected medium (0.7% of Yeast Nitrogen Base, 0.5% of casamino acids and 1% of glucose). After 48 hours of culture, cells and supernatant are separated by centrifugation and the thrombin-inhibitory activity is determined in the supernatant using the colorimetric test (proteolytic activity on a synthetic substrate, chromozyme TH—Boehringer Mannheim). Table I presents the results of the assays; each value corresponds to the mean of two independent experiments. The rHV2Lys47 activity is expressed in ATU/ml of supernatant.

TABLE I

| Plasmid | ATU/ml |
|---|---|
| pTG3894 | 40 |
| pTG3864 | 50 |
| pTG3867 | 130 |
| pTG3884 | 125 |

In all cases, anti-thrombin activity is detected. The rHV2Lys47 protein produced by the yeast is hence excreted into the supernatant. Furthermore, it is secreted in active form. The best results are obtained with the strains transformed by pTG3884 and pTG3867.

The protein content of the supernatants is analyzed by HPLC. The major peak obtained corresponds well to that of rHV2Lys47 (in its 65-amino acid form), and determination of the N-terminal sequence confirms the production of a correctly synthesized molecule.

EXAMPLE 3

Construction of a Vector for the Expression of Insect Defensin A: pTG4826

A. Synthesis of a DNA sequence coding for insect defensin A.

The synthesis is carried out in two blocks assembled by means of their KpnI cohesive ends. The first block comprises 3 oligonucleotides numbered from 1 to 3, and the second block, 6 oligonucleotides numbered from 4 to 9. Their sequence and the position of the oligonucleotides [SEQ ID NOS.:29–37] (last line of the table; the circles represent the 5' portion of the oligonucleotide) are given in Table II

TABLE II

| No. | Sequence |
|---|---|
| 1 | 5' AGCTTGGACAAGAGAGCTACCTGTGACTTGTTGTCCGGTAC |
| 2 | 5' GGTAGCTCTCTTGTCCA |
| 3 | 5' CGGACAACAAGTCACA |
| 4 | 5' CGGTATTAACCACTCCGCTTGTGCTGCTCACTGTTTGTTG |
| 5 | 5' AGCACAAGCGGAGTGGTTAATACCGGTAC |
| 6 | 5' AGAGGTAACAGAGGTGGCTACTGTAACGGTAAGGGTGT |
| 7 | 5' AGTAGCCACCTCTGTTACCTCTCAACAAACAGTGAGC |
| 8 | 5' TTGTGTTTGTAGAAACTAAGGATCCG |
| 9 | 5' AATTCGGATCCTTAGTTTCTACAAACACAAACACCCTTACCGTTAC |

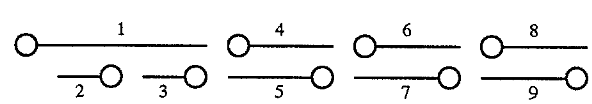

The sequence [SEQ ID NOS.: 38–39] obtained is as follows:

```
HindIII                +1                                  KpnI
10
AGC TTG GAC AAG AGA GCT ACC TGT GAC TTG TTG TCC GGT ACC
                    Ala Thr Cys Asp Leu Leu Ser Gly Thr 20
GGT ATT AAC CAC TCC GCT TGT GCT GCT CAC TGT TTG TTG AGA
Gly Ile Asn His Ser Ala Cys Ala Ala His Cys Leu Leu Arg
```

```
                30
GGT AAC AGA GGT GGC TAC TGT AAC GGT AAG GGT GTT TGT GTT
Gly Asn Arg Gly Gly Tyr Cys Asn Gly Lys Gly Val Cys Val

40          BamHI-EcoRI
TGT AGA AAC TAA GGATCCG
Cys Arg Asn
```

The synthesis of the first block employs the oligonucleotides 4, 5, 6, 7, 8 and 9, and is performed in the following manner:

oligonucleotides 5, 6, 7 and 8 are first phosphorylated at their 5' ends to avoid the formation of polymers during assembling. For each of these oligonucleotides, 100 picomoles are treated with polynucleotide kinase, 2 units in a final volume of 20 µl of 60 µM Tris-HCl, pH 7.5, 10 µM MgCl$_2$ and 8 µM dithiothreitol (kination buffer) containing 3.3 picomoles of ATP7-labeled with $^{32}$P (5000 Ci/mmol). After 15 minutes' incubation at 37° C., 5 µmol of unlabeled ATP are added.

after incubation at 37° C. for 30 min, 75 picomoles of the oligonucleotides 5, 6, 7 and 8 are mixed and heated to 95° C. for 3 min, and the oligonucleotides 4 and 9 are then added in a final volume of 90 µmol of kination buffer described above. The mixture is heated to 95° C. for 3 minutes and then cooled slowly in the space of 2 hours to 37° C.

25 picomoles of these hybridized oligonucleotides are subjected to treatment with T4 ligase for one hour at 15° C. This reaction mixture (1 picomole) is then added to 50 ng of the of the (sic) bacteriophage M13TG131 [Kieny M. P. et al. (1983) Gene 26, 91–99] treated with EcoRI and KpnI (1 hour at 15° C.). The ligation mixture is used for transforming competent cells of E. coli strain JM103 [Messing, J. et al. (1981), Nucleic Acid Res. 9, 309]. A clone possessing the desired sequence is isolated; it is referred to as M13TG3821.

The synthesis of the second block employs the oligonucleotides 1, 2 and 3, and is performed according to the same procedure as that described for the synthesis of the first block. In this case, only the oligonucleotide 2 is phosphorylated at its 5' end.

This second block is cloned between HindII and KpnI sites of the bacteriophage M13TG3821, and a clone carrying the DNA sequence coding for defensin A (FIG. 5) is isolated; it is referred to as M13TG3849.

B. Construction of the plasmid for the expression of defensin A: pTG4839.

The SphI-SmaI fragment of 1045 base pairs of the bacteriophage M13TG3846 described above (Example 1, E.) is transferred into the vector M13TG3869 described above (Example 1, D.) digested beforehand with SphI and SmaI. The vector M13TG4803 which carries:

the promoter of the MFα1 gene, followed by an ATG codon, the sequence XII, the mutated "pro" sequence of the MFα1 gene followed by the codons coding for Lys-Arg, the sequence coding for rHV2Lys47 is thereby obtained.

In order to replace the sequence coding for rHV2Lys47 by that coding for insect defensin A, a HindIII site is introduced into the sequence coding for mutated "pro" of MFα1 using the oligonucleotide of sequence [SEQ ID NO.:40]:

5' GAAGGGGTAAGCTTGGATAAA

The HindIII-BamHI fragment of M13TG3849 described above (Example 3, A.), which carries the synthetic sequence coding for defensin A, is then introduced into this vector treated beforehand with HindIII and BamHI to remove the sequence coding for rHV2Lys47.

The SphI-SalI fragment of M13TG4813 is introduced into plasmid pTG3828 (FIG. 4) opened at the SphI and SalI sites, to give the expression vector pTG4839, which contains:

the sequence of the URA3 gene from which its promoter has been deleted (URA3-d), the promoter of the MFα1 gene, followed by an ATG, the sequence XII, the mutated "pro" sequence of the MFα1 gene followed by the codons coding for Lys-Arg, the synthetic sequence coding for insect defensin A, the terminator of the gene coding for PGK of yeast, a fragment of pBR322, a fragment of the 2µ plasmid.

EXAMPLE 4

Production of Defensin A in the Culture Supernatant

A yeast strain of the species Saccharomyces cerevisiae of genotype MATα, ura3-251,-373,-328, leu2-3,-112, his3, pep4-3 is transformed with plasmid pTG4839 by the lithium acetate method [Ito, H. et al. J. Bactériol. (1983) 153: 163] and the Ura+ prototrophs are selected. They are then cultured in an Erlenmeyer at 30° C. on a selective medium (0.7% of Yeast Nitrogen Base, 0.5% of casamino acids and 1% of glucose). After 48 hours of culture, cells and supernatant are separated by centrifugation and the supernatant is filtered through a 22µ filter and then passed through a Sep-Pak C18 cartridge. The bound material is eluted with 60% acetonitrile, 0.1% trifluoroacetic acid in water and dried under vacuum. The defensin A antibacterial activity is then demonstrated by a plating test on agar or on agarose inoculated with bacterial microorganisms (Micrococcus luteus) in accordance with the procedure described by Lambert et al. (1989) PNAS 86: 262–266.

In the supernatant of yeasts transformed by plasmid pTG4839, antibacterial activity is indeed detected. The defensin A protein produced by the yeast is hence excreted into the supernatant. Furthermore, it is secreted in active form.

The protein content of the supernatants is analyzed by HPLC. The major peak obtained corresponds well to that of insect defensin A, and determination of the protein sequence confirms the production of a correctly synthesized molecule.

We claim:

1. An isolated DNA fragment comprising a DNA sequence which codes for a peptide comprising the amino acid sequence (III) (SEQ ID NO:5) $R_1$-$R_2$-$R_3$-Thr-Thr-$R_4$-Ala-Thr-Ala-Ala-Thr-Ala-Leu-Phe-Phe-Thr-Ala-$R_5$-$R_6$ in which $R_1$ is an amino acid selected from Arg and Lys $R_2$ and $R_6$ are each an amino acid selected independently from Ala, Asn, Cys, Gln, Gly, His, Ile, Leu, Met, Phe, Pro, Ser, Thr, Trp, Tyr, and Val, $R_3$ and $R_5$ are each an amino acid selected independently from Asp, Gly, Asn, Pro, and Ser, and $R_4$ is an amino acid selected from Val, Leu, Ala, Cys, Phe, Ile and Met, wherein the peptide acts as a signal sequence.

2. A DNA fragment according to claim 1, which codes for a peptide comprising the amino acid sequence (IV) (SEQ ID NO:6) $R_1$-$R_2$-$R_3$-Thr-Thr-$R_4$-Ala-Thr-Ala-Ala-Thr-Ala-Leu-Phe-Phe-Thr-Ala-$R_5$-$R_6$-$R_7$, in which $R_1$ is an amino acid selected from Arg and Lys $R_2$ and $R_6$ are each an amino acid selected independently from Ala, Asn, Cys, Gln, Gly, His, Ile, Leu, Met, Phe, Pro, Ser, Thr, Trp, Tyr, and Val, $R_3$ and $R_5$ are each an amino acid selected independently from Asp, Gly, Asn, Pro, and Ser, $R_4$ is an amino acid selected from Val, Leu, Ala, Cys, Phe, Ile and Met, and $R_7$ is a proteolysis sequence $R_8$-$R_9$-$R_{10}$, in which $R_8$ is an amino acid selected from Ala, Val, Ser, Cys, Gly, Ile, Leu, and Thr, $R_9$ is an amino acid selected from Ala, Arg, Cys, Gln, Gly, His, Ile, Leu, Met, Phe, Pro, Ser, Thr, Trp, Tyr, and Val and $R_{10}$ is an amino acid selected from Ala, Cys, Gly, Leu, Pro, Gln, Ser, and Thr.

3. A DNA fragment according to claim 2, in which $R_8$ is an amino acid selected from Ala and Val and $R_{10}$ is Ala.

4. A DNA fragment according to claim 1, which codes for a peptide comprising an amino acid sequence selected from the amino acid sequences (V) and (VI)

Arg-Phe-Ser-Thr-Thr-Leu-Ala-Thr-Ala-Ala-Thr-Ala-Leu-Phe-Phe-Thr-Ala-Ser-Gln    (V) (SEQ ID NO:4)

and

Arg-Phe-Ser-Thr-Thr-Val-Ala-Thr-Ala-Ala-Thr-Ala-Leu-Phe-Phe-Thr-Ala-Ser-Gln    (VI) (SEQ ID NO:7).

5. A DNA fragment according to claim 1, which codes for a peptide comprising an amino acid sequence selected from the amino acid sequences of formula (VII) and (VIII)

Arg-Phe-Ser-Thr-Thr-Leu-Ala-Thr-Ala-Ala-Thr-Ala-Leu-Phe-Phe-Thr-Ala-Ser-Gln-$R_7$,    (VII) (SEQ ID NO:8)

and

Arg-Phe-Ser-Thr-Thr-Val-Ala-Thr-Ala-Ala-Thr-Ala-Leu-Phe-Phe-Thr-Ala-Ser-Gln-$R_7$,    (VIII) (SEQ ID NO:9)

in which $R_7$ is a proteolysis sequence $R_8$-$R_9$-$R_{10}$, in which $R_8$ is an amino acid selected from Ala, Val, Ser, Cys, Gly, Ile, Leu, and Thr, $R_9$ is an amino acid selected from Ala, Arg, Cys, Gln, Gly, His, Ile, Leu, Met, Phe, Pro, Ser, Thr, Trp, Tyr, and Val and $R_{10}$ is an amino acid selected from Ala, Cys, Gly, Leu, Pro, Gln, Ser, and Thr.

6. A DNA fragment according to claim 5, which codes for a peptide comprising an amino acid sequence selected from the amino acid sequences of formula (VII) (SEQ ID NO:10) and (VIII) (SEQ ID NO:11) in which $R_7$ is Val-Ser-Ala.

7. A cassette for the expression of a heterologous protein, comprising at least:

(a) a DNA fragment containing transcription and translation initiation signals, (b) a DNA fragment according to claim 1, and (c) a DNA fragment coding for the mature heterologous protein.

8. A cassette according to claim 7, comprising, in addition, a DNA fragment b') coding for a "pro" peptide fragment wherein fragment b') is located between fragments b) and c).

9. A cassette according to claim 8, comprising a DNA fragment b') coding for a "pro" peptide fragment having as its sequence (SEQ ID NO:17) Ala Pro Gly Leu Leu Phe Ile Asn Thr Thr Ile Ala Ser Ile Ala Ala Lys Glu Glu Gly Val Ser Leu Asp Lys Arg.

10. A cassette according to claim 7, wherein the fragment a) contains a promoter which is functional in a yeast cell and an ATG translation codon.

11. An expression cassette according to claim 7, wherein the DNA fragment c) codes for a hirudin.

12. An expression cassette according to claim 11, wherein the DNA fragment c) codes for the hirudin variant rHV2Lys47.

13. An expression cassette according to claim 7, wherein the DNA fragment c) codes for an insect defensin.

14. An expression cassette according to claim 13, wherein the DNA fragment c) codes for defensin A.

15. A plasmid vector comprising an expression cassette according to claim 7.

16. A plasmid vector according to claim 15, further comprising the origin of replication of the 2μ plasmid of yeast.

17. A plasmid vector according to claim 15, further comprising, as a selectable gene, the URA3 gene from which the URA3 promoter has been deleted.

18. A cell transformed by a plasmid vector comprising a DNA fragment according to claim 1.

19. A yeast cell according to claim 18.

20. A process for the preparation of a heterologous protein, wherein a cell according to claim 18 is cultured and wherein the protein is recovered from the culture medium.

21. A process according to claim 20, characterized in that the cell is a yeast cell.

22. A process according to claim 20, characterized in that the said protein is a hirudin.

23. A process according to claim 20, characterized in that the said protein is an insect defensin.

24. A cell transformed by a plasmid vector, which has integrated in it genome an expression cassette according to claim 7.

25. A eukaryotic cell transformed by a plasmid vector comprising a DNA fragment according to claim 1.

* * * * *

SEQUENCE LISTING ( 1 ) GENERAL INFORMATION:

( i i i ) NUMBER OF SEQUENCES: 40

( 2 ) INFORMATION FOR SEQ ID NO:1:

( i ) SEQUENCE CHARACTERISTICS:
( A ) LENGTH: 19 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:1:

Met Arg Phe Pro Ser Ile Phe Thr Ala Val Leu Phe Ala Ala Ser Ser
1               5                   10                  15

Ala Leu Ala ( 2 ) INFORMATION FOR SEQ ID NO:2:

( i ) SEQUENCE CHARACTERISTICS:
( A ) LENGTH: 64 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:2:

Ala Pro Val Asn Thr Thr Thr Glu Asp Glu Thr Ala Gln Ile Pro Ala
1               5                   10                  15

Glu Ala Val Ile Gly Tyr Ser Asp Leu Glu Gly Asp Phe Asp Val Ala
                20                  25                  30

Val Leu Pro Phe Ser Asn Ser Thr Asn Asn Gly Leu Leu Phe Ile Asn
            35                  40                  45

Thr Thr Ile Ala Ser Ile Ala Ala Lys Glu Glu Gly Val Ser Leu Asp
        50                  55                  60

( 2 ) INFORMATION FOR SEQ ID NO:3:

( i ) SEQUENCE CHARACTERISTICS:
( A ) LENGTH: 22 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:3:

Arg Phe Ser Thr Thr Leu Ala Thr Ala Ala Thr Ala Leu Phe Phe Thr
1               5                   10                  15

Ala Ser Gln Val Ser Ala
                20

( 2 ) INFORMATION FOR SEQ ID NO:4:

( i ) SEQUENCE CHARACTERISTICS:
( A ) LENGTH: 19 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:4:

Arg Phe Ser Thr Thr Leu Ala Thr Ala Ala Thr Ala Leu Phe Phe Thr
1               5                   10                  15

Ala Ser Gln ( 2 ) INFORMATION FOR SEQ ID NO:5:

( i ) SEQUENCE CHARACTERISTICS:
        ( A ) LENGTH: 19 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Peptide
        ( B ) LOCATION: 1
        ( D ) OTHER INFORMATION: /note= "Amino acid 1 is R1 which is
            selected from Arg and Lys."

( i x ) FEATURE:
        ( A ) NAME/KEY: Peptide
        ( B ) LOCATION: 2
        ( D ) OTHER INFORMATION: /note= "Amino acid 2 is R2 which is
            selected from Ala, Asn, Cys, Gln, Gly, His, Ile,
            Leu, Met, Phe, Pro, Ser, Thr, Trp, Tyr and Val."

( i x ) FEATURE:
        ( A ) NAME/KEY: Peptide
        ( B ) LOCATION: 3
        ( D ) OTHER INFORMATION: /note= "Amino acid 3 is R3 which is
            selected from Asp, Gly, Asn, Pro and Ser."

( i x ) FEATURE:
        ( A ) NAME/KEY: Peptide
        ( B ) LOCATION: 6
        ( D ) OTHER INFORMATION: /note= "Amino acid 6 is R4 which is
            selected from Val, Leu, Ala, Cys, Phe, Ile and
            Met."

( i x ) FEATURE:
        ( A ) NAME/KEY: Peptide
        ( B ) LOCATION: 18
        ( D ) OTHER INFORMATION: /note= "Amino acid 18 is R5 which
            is selected from Asp, Gly, Asn, Pro and Ser."

( i x ) FEATURE:
        ( A ) NAME/KEY: Peptide
        ( B ) LOCATION: 19
        ( D ) OTHER INFORMATION: /note= "Amino acid 19 is R6 which
            is selected from Ala, Asn, Cys, Gln, Gly, His,
            Ile, Leu, Met, Phe, Pro, Ser, Thr, Trp, Tyr and Val."

( x i ) SEQUENCE DESCRIPTION: SEQ ID NO:5:

Xaa Xaa Xaa Thr Thr Xaa Ala Thr Ala Ala Thr Ala Leu Phe Phe Thr
1               5                   10                  15

Ala Xaa Xaa ( 2 ) INFORMATION FOR SEQ ID NO:6:

( i ) SEQUENCE CHARACTERISTICS:
        ( A ) LENGTH: 22 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Peptide
        ( B ) LOCATION: 1
        ( D ) OTHER INFORMATION: /note= "Amino acid 1 is R1 which is
            selected from Arg and Lys."

( i x ) FEATURE:
    ( A ) NAME/KEY: Peptide
    ( B ) LOCATION: 2
    ( D ) OTHER INFORMATION: /note= "Amino acid 2 is R2 which is
        selected from Ala, Asn, Cys, Gln, Gly, His, Ile,
        Leu, Met, Phe, Pro, Ser, Thr, Trp, Tyr and Val."

( i x ) FEATURE:
    ( A ) NAME/KEY: Peptide
    ( B ) LOCATION: 3
    ( D ) OTHER INFORMATION: /note= "Amino acid 3 is R3 which is
        selected from Asp, Gly, Asn, Pro and Ser."

( i x ) FEATURE:
    ( A ) NAME/KEY: Peptide
    ( B ) LOCATION: 6
    ( D ) OTHER INFORMATION: /note= "Amino acid 6 is R4 which is
        selected from Val, Leu, Ala, Cys, Phe, Ile and
        Met."

( i x ) FEATURE:
    ( A ) NAME/KEY: Peptide
    ( B ) LOCATION: 18
    ( D ) OTHER INFORMATION: /note= "Amino acid 18 is R5 which
        is selected from Asp, Gly, Asn, Pro and Ser."

( i x ) FEATURE:
    ( A ) NAME/KEY: Peptide
    ( B ) LOCATION: 19
    ( D ) OTHER INFORMATION: /note= "Amino acid 19 is R6 which
        is selected from Ala, Asn, Cys, Gln, Gly, His,
        Ile, Leu, Met, Phe, Pro, Ser, Thr, Trp, Tyr and Val."

( i x ) FEATURE:
    ( A ) NAME/KEY: Peptide
    ( B ) LOCATION: 20
    ( D ) OTHER INFORMATION: /note= "Amino acid 20 is R8 which
        is selected from Ala, Val, Ser, Cys, Gly, Ile, Leu
        and Thr."

( i x ) FEATURE:
    ( A ) NAME/KEY: Peptide
    ( B ) LOCATION: 21
    ( D ) OTHER INFORMATION: /note= "Amino acid 21 is R9 which
        is selected from Ala, Arg, Cys, Gln, Gly, His,
        Ile, Leu, Met, Phe, Pro, Ser, Thr, Trp, Tyr and Val."

( i x ) FEATURE:
    ( A ) NAME/KEY: Peptide
    ( B ) LOCATION: 22
    ( D ) OTHER INFORMATION: /note= "Amino acid 22 is R10 which
        is selected from Ala, Cys, Gly, Leu, Pro, Gln, Ser
        and Thr."

( x i ) SEQUENCE DESCRIPTION: SEQ ID NO:6:

Xaa Xaa Xaa Thr Thr Xaa Ala Thr Ala Ala Thr Ala Leu Phe Phe Thr
1               5                   10                  15

Ala Xaa Xaa Xaa Xaa Xaa
            20

( 2 ) INFORMATION FOR SEQ ID NO:7:

( i ) SEQUENCE CHARACTERISTICS:
        ( A ) LENGTH: 19 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:7:

Arg Phe Ser Thr Thr Val Ala Thr Ala Ala Thr Ala Leu Phe Phe Thr
1               5                   10                  15

Ala Ser Gln ( 2 ) INFORMATION FOR SEQ ID NO:8:

( i ) SEQUENCE CHARACTERISTICS:
        ( A ) LENGTH: 22 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Peptide
        ( B ) LOCATION: 20
        ( D ) OTHER INFORMATION: /note= "Amino acid 20 is R8 which
            is selected from Ala, Val, Ser, Cys, Gly, Ile, Leu
            and Thr."

( i x ) FEATURE:
        ( A ) NAME/KEY: Peptide
        ( B ) LOCATION: 21
        ( D ) OTHER INFORMATION: /note= "Amino acid 21 is R9 which
            is selected from Ala, Arg, Cys, Gln, Gly, His, Ile, Leu,
            Phe, Pro, Ser, Thr, Trp, Tyr and Val."

( i x ) FEATURE:
        ( A ) NAME/KEY: Peptide
        ( B ) LOCATION: 22
        ( D ) OTHER INFORMATION: /note= "Amino acid 22 is R10 which
            is selected from Ala, Cys, Gly, Leu, Pro, Gln, Ser
            and Thr."

( x i ) SEQUENCE DESCRIPTION: SEQ ID NO:8:

```
Arg Phe Ser Thr Thr Leu Ala Thr Ala Ala Thr Ala Leu Phe Phe Thr
  1               5                  10                  15
Ala Ser Gln Xaa Xaa Xaa
            20
```

( 2 ) INFORMATION FOR SEQ ID NO:9:

( i ) SEQUENCE CHARACTERISTICS:
        ( A ) LENGTH: 22 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Peptide
        ( B ) LOCATION: 20
        ( D ) OTHER INFORMATION: /note= "Amino acid 20 is R8 which
            is selected from Ala, Val, Ser, Cys, Gly, Ile, Leu
            and Thr."

( i x ) FEATURE:
        ( A ) NAME/KEY: Peptide
        ( B ) LOCATION: 21
        ( D ) OTHER INFORMATION: /note= "Amino acid 21 is R9 which
            is selected from Ala, Arg, Cys, Gln, Gly, His, Ile, Leu,
            Met, Phe, Pro, Ser, Thr, Trp, Tyr and Val."

( i x ) FEATURE:
        ( A ) NAME/KEY: Peptide
        ( B ) LOCATION: 22
        ( D ) OTHER INFORMATION: /note= "Amino acid 22 is R10 which
            is selected from Ala, Cys, Gly, Leu, Pro, Gln, Ser
            and Thr."

( x i ) SEQUENCE DESCRIPTION: SEQ ID NO:9:

```
Arg Phe Ser Thr Thr Val Ala Thr Ala Ala Thr Ala Leu Phe Phe Thr
  1               5                  10                  15
Ala Ser Gln Xaa Xaa Xaa
            20
```

( 2 ) INFORMATION FOR SEQ ID NO:10:

( i ) SEQUENCE CHARACTERISTICS:
        ( A ) LENGTH: 57 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:10:

```
CGTTTCTCTA CTACAGTCGC TACTGCAGCT ACTGCGCTAT TTTTCACAGC CTCCCAA        57
```

( 2 ) INFORMATION FOR SEQ ID NO:11:

( i ) SEQUENCE CHARACTERISTICS:
        ( A ) LENGTH: 57 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:11:

```
CGTTTCTCTA CTACACTCGC TACTGCAGCT ACTGCGCTAT TTTTCACAGC CTCCCAA        57
```

( 2 ) INFORMATION FOR SEQ ID NO:12:

( i ) SEQUENCE CHARACTERISTICS:
        ( A ) LENGTH: 66 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:12:

```
CGTTTCTCTA CTACAGTCGC TACTGCAGCT ACTGCGCTAT TTTTCACAGC CTCCCAAGTT     60

TCAGCT                                                                66
```

( 2 ) INFORMATION FOR SEQ ID NO:13:

( i ) SEQUENCE CHARACTERISTICS:
        ( A ) LENGTH: 66 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:13:

```
CGTTTCTCTA CTACACTCGC TACTGCAGCT ACTGCGCTAT TTTTCACAGC CTCCCAAGTT     60

TCAGCT                                                                66
```

( 2 ) INFORMATION FOR SEQ ID NO:14:

( i ) SEQUENCE CHARACTERISTICS:
        ( A ) LENGTH: 24 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:14:

```
Ala Pro Gly Leu Leu Phe Ile Asn Thr Thr Ile Ala Ser Ile Ala Ala
 1               5                  10                  15
```

```
        Lys  Glu  Glu  Gly  Val  Ser  Leu  Asp
                       20
```

( 2 ) INFORMATION FOR SEQ ID NO:15:

( i ) SEQUENCE CHARACTERISTICS:
        ( A ) LENGTH: 26 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:15:

```
    Ala  Pro  Gly  Leu  Leu  Phe  Ile  Asn  Thr  Thr  Ile  Ala  Ser  Ile  Ala  Ala
     1              5                        10                       15

Lys  Glu  Glu  Gly  Val  Ser  Leu  Asp  Lys  Arg
                   20                       25
```

( 2 ) INFORMATION FOR SEQ ID NO:16:

( i ) SEQUENCE CHARACTERISTICS:
        ( A ) LENGTH: 40 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:16:

```
    Ala  Thr  Cys  Asp  Leu  Leu  Ser  Gly  Thr  Gly  Ile  Asn  His  Ser  Ala  Cys
     1              5                        10                       15

Ala  Ala  His  Cys  Leu  Leu  Arg  Gly  Asn  Arg  Gly  Gly  Tyr  Cys  Asn  Gly
                   20                        25                       30

Lys  Gly  Val  Cys  Val  Cys  Arg  Asn
                   35                   40
```

( 2 ) INFORMATION FOR SEQ ID NO:17:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:17:

```
CAATGAAAAA  TGGTCGACTA  TCAATCATAG                                              30
```

( 2 ) INFORMATION FOR SEQ ID NO:18:

( i ) SEQUENCE CHARACTERISTICS:
        ( A ) LENGTH: 41 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:18:

```
GACGGCCAGT  AGAATTGGCA  TGCTATTGAT  AAGATTTAAA  G                               41
```

( 2 ) INFORMATION FOR SEQ ID NO:19:

( i ) SEQUENCE CHARACTERISTICS:
        ( A ) LENGTH: 37 base pairs (B) TYPE: nucleic acid
    (C) STRANDEDNESS: single
    (D) TOPOLOGY: linear (ii) MOLECULE TYPE: DNA (genomic)

(xi) SEQUENCE DESCRIPTION: SEQ ID NO:19:

CTCCGCATTA GCTGCTCCCG GGTTATTGTT TATAAAT 37

(2) INFORMATION FOR SEQ ID NO:20:

(i) SEQUENCE CHARACTERISTICS:
    (A) LENGTH: 41 base pairs
    (B) TYPE: nucleic acid
    (C) STRANDEDNESS: single
    (D) TOPOLOGY: linear (ii) MOLECULE TYPE: DNA (genomic)

(xi) SEQUENCE DESCRIPTION: SEQ ID NO:20:

AATATAAACG ATTAAAAGGA TCCGATTTCC TTCAATTTTT A 41

(2) INFORMATION FOR SEQ ID NO:21:

(i) SEQUENCE CHARACTERISTICS:
    (A) LENGTH: 45 base pairs
    (B) TYPE: nucleic acid
    (C) STRANDEDNESS: single
    (D) TOPOLOGY: linear (ii) MOLECULE TYPE: DNA (genomic)

(xi) SEQUENCE DESCRIPTION: SEQ ID NO:21:

GATCCGTTTC TCTACTACAG TCGCTACTGC AGCTACTGCG CTATT 45

(2) INFORMATION FOR SEQ ID NO:22:

(i) SEQUENCE CHARACTERISTICS:
    (A) LENGTH: 23 base pairs
    (B) TYPE: nucleic acid
    (C) STRANDEDNESS: single
    (D) TOPOLOGY: linear (ii) MOLECULE TYPE: DNA (genomic)

(xi) SEQUENCE DESCRIPTION: SEQ ID NO:22:

GTAGCGACTG TAGTAGTGAA ACG 23

(2) INFORMATION FOR SEQ ID NO:23:

(i) SEQUENCE CHARACTERISTICS:
    (A) LENGTH: 31 base pairs
    (B) TYPE: nucleic acid
    (C) STRANDEDNESS: single
    (D) TOPOLOGY: linear (ii) MOLECULE TYPE: DNA (genomic)

(xi) SEQUENCE DESCRIPTION: SEQ ID NO:23:

TTTCACAGCC TCCCAAGTTT CAGCTGCTCC C 31

(2) INFORMATION FOR SEQ ID NO:24:

(i) SEQUENCE CHARACTERISTICS:
    (A) LENGTH: 49 base pairs
    (B) TYPE: nucleic acid
    (C) STRANDEDNESS: single
    (D) TOPOLOGY: linear (ii) MOLECULE TYPE: DNA (genomic)

( x i ) SEQUENCE DESCRIPTION: SEQ ID NO:24:

GGGAGCAGCT GAAACTTGGG AGGCTGTGAA AAATAGCGCA GTAGCTGCA    49

( 2 ) INFORMATION FOR SEQ ID NO:25:

( i ) SEQUENCE CHARACTERISTICS:
        ( A ) LENGTH: 40 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:25:

AATATAAACG ATTAAAAGAA TGCGTTTCTC TACTACAGTC    40

( 2 ) INFORMATION FOR SEQ ID NO:26:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:26:

GCCTCCCAAG TTTCAGCTAT TACGTATACA GACTGC    36

( 2 ) INFORMATION FOR SEQ ID NO:27:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:27:

TCCGCATTAG CTGCTCCCGG GAACACTACA ACAGAA    36

( 2 ) INFORMATION FOR SEQ ID NO:28:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:28:

GTTTCTCTAC TACACTCGCT ACTGC    25

( 2 ) INFORMATION FOR SEQ ID NO:29:

( i ) SEQUENCE CHARACTERISTICS:
        ( A ) LENGTH: 41 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:29:

AGCTTGGACA AGAGAGCTAC CTGTGACTTG TTGTCCGGTA C    41

( 2 ) INFORMATION FOR SEQ ID NO:30:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:30:

GGTAGCTCTC TTGTCCA                      17

( 2 ) INFORMATION FOR SEQ ID NO:31:

( i ) SEQUENCE CHARACTERISTICS:
        ( A ) LENGTH: 16 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:31:

CGGACAACAA GTCACA                      16

( 2 ) INFORMATION FOR SEQ ID NO:32:

( i ) SEQUENCE CHARACTERISTICS:
        ( A ) LENGTH: 40 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:32:

CGGTATTAAC CACTCCGCTT GTGCTGCTCA CTGTTTGTTG      40

( 2 ) INFORMATION FOR SEQ ID NO:33:

( i ) SEQUENCE CHARACTERISTICS:
        ( A ) LENGTH: 29 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:33:

AGCACAAGCG GAGTGGTTAA TACCGGTAC             29

( 2 ) INFORMATION FOR SEQ ID NO:34:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:34:

AGAGGTAACA GAGGTGGCTA CTGTAACGGT AAGGGTGT        38

( 2 ) INFORMATION FOR SEQ ID NO:35:

( i ) SEQUENCE CHARACTERISTICS:
        ( A ) LENGTH: 37 base pairs (B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:35:

```
AGTAGCCACC TCTGTTACCT CTCAACAAAC AGTGAGC                                    37
```

(2) INFORMATION FOR SEQ ID NO:36:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:36:

```
TTGTGTTTGT AGAAACTAAG GATCCG                                                26
```

(2) INFORMATION FOR SEQ ID NO:37:

(i) SEQUENCE CHARACTERISTICS:
        (A) LENGTH: 46 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:37:

```
AATTCGGATC CTTAGTTTCT ACAAACACAA ACACCCTTAC CGTTAC                          46
```

(2) INFORMATION FOR SEQ ID NO:38:

(i) SEQUENCE CHARACTERISTICS:
        (A) LENGTH: 145 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: CDS
        (B) LOCATION: 16..135

(xi) SEQUENCE DESCRIPTION: SEQ ID NO:38:

```
AGCTTGGACA AGAGA GCT ACC TGT GAC TTG TTG TCC GGT ACC GGT ATT AAC            51
                Ala Thr Cys Asp Leu Leu Ser Gly Thr Gly Ile Asn
                 1               5                  10

CAC TCC GCT TGT GCT GCT CAC TGT TTG TTG AGA GGT AAC AGA GGT GGC             99
His Ser Ala Cys Ala Ala His Cys Leu Leu Arg Gly Asn Arg Gly Gly
         15                  20                  25

TAC TGT AAC GGT AAG GGT GTT TGT GTT TGT AGA AAC TAAGGATCCG                 145
Tyr Cys Asn Gly Lys Gly Val Cys Val Cys Arg Asn
         30                  35                  40
```

(2) INFORMATION FOR SEQ ID NO:39:

(i) SEQUENCE CHARACTERISTICS:
        (A) LENGTH: 40 amino acids
        (B) TYPE: amino acid
        (C) STRANDEDNESS: single
        (D) TOPOLOGY: linear (ii) MOLECULE TYPE: protein -continued (xi) SEQUENCE DESCRIPTION: SEQ ID NO:39:

Ala Thr Cys Asp Leu Leu Ser Gly Thr Gly Ile Asn His Ser Ala Cys
1               5                   10                  15

Ala Ala His Cys Leu Leu Arg Gly Asn Arg Gly Gly Tyr Cys Asn Gly
            20                  25                  30

Lys Gly Val Cys Val Cys Arg Asn
        35              40

(2) INFORMATION FOR SEQ ID NO:40:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:40:

GAAGGGGTAA GCTTGGATAA A           21